(12) United States Patent
Redaelli

(10) Patent No.: US 9,707,160 B2
(45) Date of Patent: Jul. 18, 2017

(54) COSMETIC COMPOSITION BASED ON A MAGNETIC OR MAGNETISABLE MATERIAL, THE PREPARATION THEREOF AND USE THEREOF FOR CLEANSING THE EPIDERMIS

(75) Inventor: Carolina Redaelli, Como (IT)

(73) Assignee: DERMOPHISIOLOGIQUE S.R.L., Caronno Pertusella (IT)

( * ) Notice: Subject to any disclaimer, the term of this patent is extended or adjusted under 35 U.S.C. 154(b) by 1222 days.

(21) Appl. No.: 12/259,724

(22) Filed: Oct. 28, 2008

(65) Prior Publication Data

US 2009/0110704 A1   Apr. 30, 2009

(30) Foreign Application Priority Data

Oct. 30, 2007   (IT) .............................. MI2007A2098

(51) Int. Cl.
| | | |
|---|---|---|
| *A61Q 19/10* | (2006.01) | |
| *A61K 8/04* | (2006.01) | |
| *A61K 8/02* | (2006.01) | |
| *A61K 8/19* | (2006.01) | |
| *A61K 8/27* | (2006.01) | |

(52) U.S. Cl.
CPC ............ *A61K 8/042* (2013.01); *A61K 8/0212* (2013.01); *A61K 8/19* (2013.01); *A61K 8/27* (2013.01); *A61Q 19/10* (2013.01); *A61K 2800/31* (2013.01); *A61K 2800/47* (2013.01)

(58) Field of Classification Search
None
See application file for complete search history.

(56) References Cited

U.S. PATENT DOCUMENTS

| | | | |
|---|---|---|---|
| 4,046,591 A | | 9/1977 | Laguerre |
| 5,011,855 A | * | 4/1991 | Traitler et al. ................. 514/558 |
| 5,234,682 A | | 8/1993 | Macchio et al. |
| 5,718,906 A | * | 2/1998 | Martin et al. .................. 424/401 |
| 5,800,835 A | | 9/1998 | Zastrow et al. |
| 6,074,385 A | * | 6/2000 | Klopotek ......................... 606/27 |
| 6,139,827 A | * | 10/2000 | Cohen et al. ............... 424/70.16 |
| 6,461,626 B1 | * | 10/2002 | Rabe et al. .................... 424/401 |
| 6,872,401 B2 | * | 3/2005 | Seyler et al. .................. 424/401 |
| 2002/0197221 A1 | * | 12/2002 | Nichols et al. .................. 424/64 |
| 2007/0166247 A1 | * | 7/2007 | Aliano et al. .................... 424/59 |
| 2008/0247977 A1 | * | 10/2008 | Le Gendre et al. ............. 424/64 |

FOREIGN PATENT DOCUMENTS

| | | | |
|---|---|---|---|
| DE | 43 25 071 A1 | | 1/1995 |
| EP | 1 043 018 A1 | | 10/2000 |
| EP | 1043019 | * | 10/2000 |
| IT | 1060139 A | | 7/1982 |
| JP | 01068313 A2 | | 3/1989 |
| JP | 07053369 A2 | | 2/1995 |
| WO | 2004/000244 A1 | | 12/2003 |
| WO | WO 2004/000244 | * | 12/2003 |
| WO | WO 2005/074867 | * | 8/2005 |

OTHER PUBLICATIONS

Machine translation of EP 1043019.*

* cited by examiner

*Primary Examiner* — Jyothsna Venkat
(74) *Attorney, Agent, or Firm* — Pearne & Gordon LLP

(57) ABSTRACT

The present invention relates to a cosmetic composition based on a magnetic or magnetizable material, the preparation thereof and use thereof for surface and deep cleansing of the epidermis. Said cosmetic composition has revealed to be particularly useful for preparing a mask for cleansing the epidermis of the face, breast, hands and body and, simultaneously, for maintaining the aesthetic appearance and functional efficiency thereof.

1 Claim, 1 Drawing Sheet

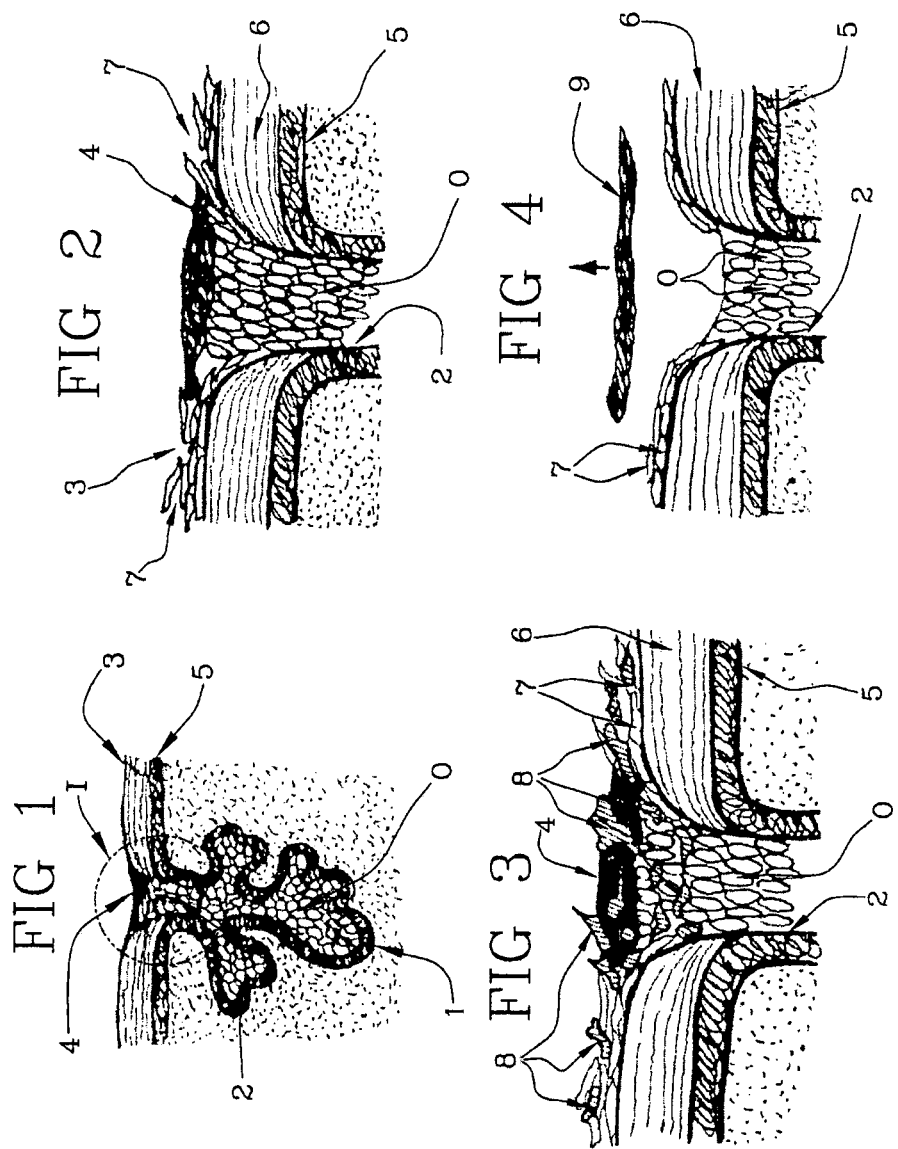

COSMETIC COMPOSITION BASED ON A MAGNETIC OR MAGNETISABLE MATERIAL, THE PREPARATION THEREOF AND USE THEREOF FOR CLEANSING THE EPIDERMIS

BACKGROUND OF THE INVENTION

The present invention relates to a cosmetic composition based on a magnetic or magnetisable material, the preparation thereof and use thereof for surface and deep cleansing of the epidermis. Said cosmetic composition has revealed to be particularly useful for preparing a mask for cleansing the epidermis of the face, breast, hands and body and, simultaneously, for maintaining the aesthetic appearance and functional efficiency thereof.

The skin's pores are minute openings, or orifices, which communicate with the cutaneous glands (sweat and sebaceous glands) through specific secretion ducts. Unfortunately, said ducts very often become partly or totally clogged by external contaminating materials. The clogging, even partial, of secretion ducts prevents the cutaneous glands from performing their functions correctly.

For example, the sebaceous glands no longer secrete the quantity of sebum necessary to lubricate the epidermis in order to prevent the skin itself from becoming dry.

The sweat glands, for their own part, no longer secrete a sufficient quantity of perspiration, the acidity of which hinders the development of harmful micro-organisms. Moreover, the correct functioning of these two glands is necessary in order to eliminate a large part of the toxins produced in the organism.

It is therefore important to keep the epidermis efficient, i.e. in a physiological condition in which the functionality of the sebaceous and sweat glands is, to the extent possible, optimal.

This applies in particular for the skin of the face, which is, generally speaking, the part of the body most exposed to harmful external agents, but also for the skin of the breast, hands and body.

Unfortunately, the cosmetic products commonly used to cleanse the skin (e.g. soaps, lotions, masks) are often unable to provide an adequate deep cleansing action. In fact, due to its anatomic configuration and physiological characteristics, the pilosebaceous follicle is never effectively reached by the application of granular or creamy products or lotions specifically intended for cleansing the skin. Moreover, said cosmetic products almost have an action that is at least partly irritating (e.g. products having an exfoliating action). Consequently, cleansing, as commonly performed, may be linked to the possible occurrence of an inflammatory state in the skin itself.

All this gives rise to the necessity of following up the cleansing with a treatment for regenerating and restoring the functionality of the epidermis and of the exocrine glands thereof.

There is hence a greatly felt need for a cosmetic product that can allow the skin's pores to be kept free of harmful clogging materials (e.g. blackheads, comedos) not only on the surface, but also deep down, and which at the same time can exert such an action in the most delicate manner possible (that is, without inducing aggressive effects of a chemical, physical, physiological or like nature, such as to provoke irritation or inflammation of the treated part).

At the same time, there is an equally felt need for a product which, besides possessing the above-described characteristics, is also able to maintain and/or restore an optimal functional state of the epidermis and of the exocrine glands thereof.

The object of the present invention is to provide an adequate answer to the needs highlighted above.

This and yet other objects, which will become apparent from the detailed description that follows, have been achieved by the Applicant, who has unexpectedly found that by incorporating a suitable magnetic or magnetisable material in a suitable, strictly non-aqueous vehicle containing suitable substances beneficial for the skin, it is possible to obtain a cosmetic product (so-called dermal magnetic product) capable of providing the desired answer to the previously described needs.

SUMMARY OF THE INVENTION

Therefore, it is an object of the present invention to provide a dermal magnetic cosmetic composition comprising a magnetic or magnetisable material stably incorporated in a strictly non-aqueous vehicle, as set forth in the appended independent claim.

It is a further object of the present invention to provide a method for preparing said dermal magnetic cosmetic composition, as described in the appended independent claim.

Still a further object of the present invention relates to the use of said cosmetic composition for cleansing the epidermis, as set forth in the appended independent claim.

Still a further object of the present invention relates to the use of the aforesaid composition for preparing a dermal magnetic mask for cleansing the skin of the face, as set forth in the appended independent claim.

Still a further object of the present invention relates to said mask, as set forth in the appended independent claim.

Another object of the present invention is to provide a cosmetic treatment method for cleansing the epidermis using the aforesaid cosmetic composition, as set forth in the appended independent claim.

Preferred embodiments of the invention are illustrated in the appended dependent claims.

BRIEF DESCRIPTION OF THE DRAWINGS

The present invention is illustrated in detail in the description that follows. By way of non-limiting example, said invention is visually illustrated with the aid of the appended Figures which show:

in FIG. 1, an axial sectional view of a pilosebaceous gland, with its duct opening on the surface of the epidermis (for illustrative convenience, the hair has not been drawn);

in FIG. 2, a view, on an enlarged scale, of region I of FIG. 1, circled;

in FIG. 3, the same view as in FIG. 2, illustrating the penetration into this region of the magnetic particles according to the invention, used for cleansing the skin;

in FIG. 4, the same view as in FIG. 3, after the removal of the previously introduced magnetic particles, which have simultaneously carried along with them the majority of dead surface cells and polluting materials present at the opening and partly inside the sebaceous duct.

DETAILED DESCRIPTION OF THE INVENTION

The dermal magnetic cosmetic composition of the present invention comprises a magnetic or magnetisable material and is characterised in that said magnetic or magnetisable material is incorporated in a strictly non-aqueous vehicle.

Said magnetic or magnetisable material consists of at least one magnetic or magnetisable substance, wherein said at least one substance is preferably selected among metals and/or the derivatives thereof, such as salts and/or oxides.

Preferably, said metals and/or derivates thereof are iron, zinc, iron oxide and/or zinc oxide.

In a preferred embodiment of the invention, the magnetic or magnetisable material consists of iron oxide ($Fe_2O_3$).

In another preferred embodiment of the invention, the magnetic or magnetisable material consists of a mixture of two or more magnetic or magnetisable substances selected from among the ones specified above.

In a particularly preferred embodiment, the magnetic or magnetisable material consists of a mixture of iron oxide ($Fe_2O_3$) and zinc oxide (ZnO).

In this latter case, however, ZnO is used specifically for its anti-inflammatory action on the skin, rather than for its magnetic properties.

In said particularly preferred mixture, $Fe_2O_3$ and ZnO are in a reciprocal ponderal ratio between 6:1 and 1:1; preferably between 5:1 and 1.5:1; more preferably, between 4:1 and 2.5:1.

The magnetic or magnetisable material of the present invention is used in the form of solid microparticles; preferably, said particles have a spherical or spheroid or ovoid shape, more preferably, irregular or with surface rugosities.

In the composition according to the invention, said microparticles of magnetic or magnetisable material have an average size ≤100μ; preferably, ≤80μ; more preferably, ≤60μ.

In a preferred embodiment of the invention, said microparticles have an average size between 10μ and 80μ; more preferably, between 20μ and 60μ: for example, around 40μ.

The aforesaid magnetic or magnetisable material is present in the composition according to the invention in a quantity ranging on average from 10% to 30% by weight, relative to the total weight of the composition.

Preferably, said material is present in a quantity between 15% and 25% by weight; more preferably, between 18% and 23% by weight; still more preferably, in a quantity between 19.5% and 21.5%; still more preferably, between 20.5% and 21%.

In a preferred embodiment of the invention, said material is present in a ponderal quantity of around 20.5% relative to the total weight of the composition.

Unlike the known art, which describes the use of a magnetic material incorporated in aqueous-based vehicles (practically speaking, water/oil emulsions in the form of a gel, (ream, milk, paste and the like. In this regard see patent IT 1060139, pag. 4), in the composition according to the present invention the vehicle in which the microparticles of a magnetic or magnetisable material are incorporated is a strictly non-aqueous vehicle. Said vehicle is substantially an anhydrous lipid gel (hereinafter referred to as an anhydrous lipogel), i.e. a composition that has the characteristics of a dense gel, despite being completely devoid of water.

Said anhydrous lipogel (characterised, on average, by a consistency similar to that of a lip balm in stick form) consists substantially of a lipid-based mixture comprising a number of non-aqueous components having different origins and functional activities.

Said components may be of vegetable or chemical origin, optionally of animal origin.

Said components as described above are preferably selected from among substances having one or more of the following functional activities: emollient, conditioning, mattifying, abrasive, adsorbent, colorant, filmogenic, emulsifying, surfactant, solvent, smoothing, lightening, soothing; transdermal vehicle; cosmetological excipient, rheological additive, said substances being added in suitable quantities such as to achieve the desired consistency of the formulation.

The anhydrous lipogel of the present invention further comprises a quantity of at least one substance having a beneficial action for the epidermis. Said beneficial action is, generally speaking, capable of maintaining and/or restoring the aesthetic appearance and/or functional efficiency of the epidermis.

Said at least one substance having a beneficial action for the epidermis is selected from among those known to have an anti-inflammatory and/or soothing action, cleansing and/or emulsifying action, restorative and/or immune balancing action and an ability to control the hydration of the skin and maintain the elasticity thereof.

Preferably, the substance having an anti-inflammatory and/or soothing action is selected from among: zinc oxide, titanium dioxide, blackcurrant oil, aloe, chamomile and mallow; more preferably, from among zinc oxide, titanium dioxide and blackcurrant oil. Preferably, the substance having a cleansing and/or emulsifying action is selected from among: beeswax, hydrogenated castor oil, soy sterols, $C_{12}$-$C_{15}$ alkyl benzoates, hydrogenated lecithin, cetearyl glucosides and $C_{12}$-$C_{20}$ PEG 8 esters; preferably from among beeswax, hydrogenated castor oil and soy sterols.

Preferably, the substance having a restorative and/or immune balancing action is selected from among: blackcurrant oil, substances rich in ω-3, ω-6 unsaturated fatty acids, ceramides, soy sterols, shea butter, beeswax, sweet almond oil and avocado oil; preferably, from among blackcurrant oil, substances rich in ω-3, ω-6 unsaturated fatty acids, ceramides, soy sterols and shea butter.

As is apparent from the previous list of examples, some of the substances that may be used for the purposes of the present invention simultaneously possess more than one of the activities specified: they can therefore be used for more than one purpose, i.e. to obtain more than on beneficial effect on the skin simultaneously.

In a preferred embodiment, the anhydrous lipogel of the present invention comprises a mixture of the above-mentioned substances. More preferably, said mixture consists of at least one anti-inflammatory and/or soothing substance selected from among those specified above, at least one cleansing and/or emulsifying substance, selected from among those specified above and at least one substance having a restorative action on the epidermis and/or immune balancing action, selected from among those specified above.

The composition of the invention may further comprise additives, excipients, coformulants, aromatising substances and/or fragrances suitable for improving the characteristics thereof.

In a particularly preferred embodiment, the cosmetic composition of the present invention comprises a quantity of microparticles of a magnetic or magnetisable material (preferably, iron oxide) stably incorporated in a lipid-based anhydrous lipogel, as previously described, wherein said lipogel also includes a mixture consisting of:

at least one substance with an anti-inflammatory and/or soothing action, selected from among those described previously: preferably, said substance is zinc oxide;

at least one substance with a cleansing and/or emulsifying action, selected from among those described previously: preferably, said substance is beeswax;

at least one substance with a restorative action on the epidermis and/or immune balancing action, selected from among those described previously: preferably, said substance is blackcurrant oil.

Preferably, in said composition zinc oxide is present in a ponderal quantity between 5% and 12% w/w, relative to the total weight of the anhydrous lipogel; preferably, between 6% and 10% w/w.

Preferably, in said composition beeswax is present in a ponderal quantity between 1% and 10% w/w, relative to the total weight of the anhydrous lipogel; preferably, between 1% and 5% w/w.

Preferably, in said composition blackcurrant oil is present in a ponderal quantity between 0.1% and 4% w/w relative to the total weight of the anhydrous lipogel; preferably, between 0.1% and 2% w/w.

The advantage conferred upon the dermal magnetic cosmetic composition of the present invention by the use of the aforesaid lipid-based anhydrous lipogel consists in the fact that said lipogel has unexpectedly shown to be capable of incorporating the magnetic material in a much more homogeneous and stable manner compared to the hydrogels or water/oil emulsions normally used. As a result, it has been advantageously possible to prevent the magnetic material incorporated in the anhydrous lipogel from coming into contact with the oxygen or humidity in the air during packaging and storage, thus avoiding oxidation phenomena. Furthermore\, said oxidation phenomena are also avoided precisely thanks to the total absence of water within the formulation (water that is obviously present, in contrast, in the water/oil emulsions of the prior known art). As a result, the magnetic material, in particular the iron-based material (e.g. iron oxide), will not rust over time.

All this has positive repercussions on the stability and hence storage life of the composition of the invention.

Furthermore, the perfectly homogeneous distribution of the magnetic material inside the lipogel allows the product to be applied in an optimal manner on the portion of skin to be treated.

Solely by way of a non-limiting example of the possible variants within the ability of a person skilled in the formulation art, an illustration is given below, in general terms, of the composition of a preferred mixture of active ingredients useful for achieving the desired anhydrous lipogel according to the invention, by suitable mixing of the components according to known methods and in suitable mixing means, commonly used in the sector.

EXAMPLE 1

Anhydrous Lipogel of the Present Invention—General Example of a Particularly Preferred Mixture of Ingredients

| | |
|---|---|
| "Cyclomethicone" | from 10% to 26% w/w; |
| "$C_{12}$-$C_{15}$ Alkyl Benzoate" | from 10% to 25% w/w; |
| "Glycine Soja Oil" | from 10% to 25% w/w; |
| "Dicaprylyl Carbonate" | from 5% to 10% w/w; |
| "PPG-5-Pentaerythrityl Ether" | from 5% to 10% w/w; |
| "Hydrated Silica" | from 5% to 10% w/w; |
| "Zinc Oxide" | from 5% to 12% w/w; |
| "cera alba" | from 1% to 10% w/w; |
| "Hydrogenated Castor Oil" | from 1% to 5% w/w; |
| "Quaternium-16-Hectorite" | from 1% to 5% w/w; |
| "alcohol denaturate" | from 0.1% to 1% w/w; |
| "Blackcurrant Oil" | from 0.1% to 4% w/w. |

The desired quantity of magnetic or magnetisable material is incorporated into this mixture to make the dermal magnetic cosmetic composition of the invention.

Solely by way of non-limiting example, in the following Example 2 an illustration is given, in general terms, of a range of possible variants of particularly preferred cosmetic compositions according to the present invention.

EXAMPLE 2

Magnetic Cosmetic Composition of the Present Invention—General Example of Preferred Composition $Fe_2O_3$: from 10% to 30% w/w;

Mixture of Example 1 (anhydrous lipogel): q.s. to 100% by weight.

EXAMPLE 3

Dermal Magnetic Cosmetic Composition of the Present Invention—General Example of Particularly Preferred Composition $Fe_2O_3$: from 20.5% to 21% w/w;

Mixture of Example 1 (anhydrous lipogel): q.s. to 100% by weight, wherein, in said mixture of Example 1, the mixture consisting of substances having a beneficial action for the epidermis contains said substances in the following percentages by weight relative to the total weight of the anhydrous lipogel:

| | |
|---|---|
| "Zinc Oxide" | from 6% to 10% w/w; |
| "cera alba" | from 1% to 5% w/w; |
| "Blackcurrant Oil" | from 0.1% to 2% w/w. |

The dermal magnetic cosmetic compositions according to the invention, such as those included in Examples 2 and 3, are prepared according to traditional methods, by mixing under mechanical agitation, at a temperature higher than or close to room temperature (preferably, the temperature is between 20° C. and 45° C.), the individual components, selected in the most appropriate percentages (known to the person skilled in the formulation art), in order to obtain the desired consistency and fluidity, in suitable containers equipped with suitable agitation and/or mixing means. There is no constraint on the order in which the individual ingredients are added. In one embodiment of the invention, the magnetic material or materials are added to the pre-formed lipogel, under constant agitation, at a temperature preferably between 20° C. and 30° C.

Preferably, mixing takes place at a speed such as to minimise the absorption of air and/or humidity from the surrounding environment. Said mixing may take place in a vacuum or in an inert anhydrous atmosphere. Preferably, a machine called vacuum turboemulsifier is used.

By way of comparative example, a general composition of a possible type of nor-anhydrous vehicle (i.e. in the form of a water/oil emulsion) known in the art is illustrated below.

EXAMPLE 4 (COMPARATIVE)

Composition of a Water/Oil Emulsion

| | |
|---|---|
| "Glycine Soja Oil" | from 26% to 50% w/w; |
| "aqua" | from 26% to 50% w/w; |
| "$C_{12-15}$ Alkyl Benzoate" | from 5% to 10% w/w; |
| "Hydrogenated Castor Oil" | from 1% to 5% w/w; |
| "cera alba" | from 1% to 5% w/w; |
| "PEG-30-dipolyhydroxystearate" | from 1% to 5% w/w; |
| "Dimethicone" | from 0.1% to 1% w/w; |
| "Capryloyl Glycine" | from 0.1% to 1% w/w; |
| "Magnesium Sulfate" | from 0.1% to 1% w/w; |
| "Citrus Grandis & Glycerin" | from 0.1% to 1% w/w; |
| "Disodium EDTA" | from 0.1% to 1% w/w; |
| "profumo/parfum" | from 0.1% to 1% w/w; |
| "Xantan Gum" | from 0.1% to 1% w/w; |
| "Tocopherol & Triethyl Citrate | from 0.1% to 1% w/w. |

It has been demonstrated that the composition obtained by incorporating the magnetic material in the water/oil emulsion of Example 4 tends to become de-emulsified, at least partly, over time, in a period of between about 20 and about 30 days.

Furthermore, said composition tends to rust after a fairly brief period of storage, ranging from about 1 to about 2 months.

In contrast, the cosmetic compositions of the invention (both those of Example 2 and those of Example 3) have demonstrated to be much more stable (they have shown no signs of de-emulsification over time); moreover, said compositions have not undergone any oxidation over time (therefore, they virtually have no determinable expiry period).

The dermal magnetic cosmetic composition of the present invention has revealed to be particularly useful in a cosmetic treatment method for surface and deep cleansing of the epidermis. In particular, said cosmetic composition has revealed to be useful for preparing a dermal magnetic mask for cleansing the epidermis of the face, breast, hands and body and, simultaneously, for maintaining the aesthetic appearance and functional efficiency thereof.

The cosmetic treatment method according to the present invention for the aforesaid cleansing of the epidermis substantially consists of the following phases:

a) at least one phase in which the magnetic composition of the invention is applied on the area of the epidermis that one desires to cleanse;

b) at least one phase in which the magnetic material is removed from the epidermis;

c) at least one phase in which the residual anhydrous lipogel (no longer magnetic) is removed from the epidermis.

In said phase a) the magnetic composition is spread/distributed over the skin area (e.g., the face) to be submitted to cleansing by performing a gentle massage; preferably, said massage is carried out with a constant circular movement for the time necessary to achieve a uniform and homogeneous distribution of the product. Generally speaking, the time required for performing the aforesaid massage is around 2-8 minutes, preferably around 3-5 minutes.

In this manner it is possible (as schematically illustrated in FIG. 3) to cause the micromagnetic particles to penetrate inside the surface layer of dead skin cells and also partly inside the sweat and sebaceous ducts.

Therefore, at the end of the application of the magnetic composition on the skin, the latter is coated with a finely homogeneous magnetic mask which, among other things, develops a magnetic field having a toning effect on the skin itself.

As a result, the skin itself is transformed into a magnetic field wherein also the dead surface cells and polluting materials, e.g. the sebum secretions that clog the pores (blackheads, comedos) have been transformed into magnetic substances, as they have intimately incorporated within them the micromagnetic particles.

Furthermore, thanks to the presence in the anhydrous lipogel of the previously described substances beneficial for the skin (preferably, of the mixture of said substances described previously), during the massage the desired action of maintaining and/or restoring the optimal functional state of the epidermis and the exocrine glands thereof will also be commenced.

In fact the zinc oxide will exert, in particular, its specific anti-inflammatory and soothing action upon the epidermis; the beeswax will exert its cleansing and emulsifying action, in particular at the level of the pilosebaceous follicle; the blackcurrant oil (containing a high quantity of $\omega$-3 and $\omega$-6 fatty acids) will exert its restorative action on the third layer of the epidermis (granular layer), possibly by restoring the cement that surrounds the corneocytes and holds them together.

Once phase a) is completed, the magnetic mask thus formed is preferably allowed to rest and act upon the skin for several minutes (e.g. for a period between about 1 and 10 min; more preferably, between 3 and 5 min), after which one may proceed to phase b).

In said phase b), the magnetic material of the mask is removed from the skin using suitable removal means consisting of a magnet Dr a magnetisable material (e.g. an electromagnet): the use of a magnet is particularly preferred.

Said magnet shall be made in such a way as to be efficient and simple to handle and clean after use.

In a preferred embodiment, said magnet shall be configured so as to follow the contour of the surface of the skin as closely as possible, e.g., like the head of a shaver.

By way of non-limiting example, a magnetic device particularly suited to the purpose of carrying out the operation of phase b) is the one described on pages 5 and 9-11 and schematically illustrated in FIGS. 5-8 of the Italian patent IT 1060139, which are specifically cited and incorporated herein by way of reference.

During phase b), the magnetic removal means (magnet or electromagnet) is made to pass repeatedly over the epidermis (e.g. with a circular movement) and removes, by attraction, all the magnetic particles and all the polluting materials intimately linked to them, which together form a magnetic pulp (as schematically illustrated in FIG. 4).

In this manner, a large part of the dead surface cells, foreign particles and excess sebum contained at the opening of the sweat and sebaceous ducts are removed together with the magnetic particles, thus freeing the ducts themselves, which will once again be able to perform their function correctly.

The desired surface and deep cleansing of the epidermis are therefore achieved in an optimal manner.

What has been described so far is schematically illustrated in FIG. 1-4.

FIG. 1 illustrates an axial cross-section view of a sebaceous gland (1) which secretes sebum (0) through the sebaceous duct (2) so as to lubricate the outer surface (3) of the epidermis, consisting of dead skin cells. (4) indicates a blackhead, which is formed by dried sebum mixed with polluting material, e.g. atmospheric dust. Indicated beneath the outer layer (3) of the epidermis is the basal layer (5), which reconstructs the epidermis.

FIG. 2 better illustrates the situation of the skin at the opening of the sebaceous duct (2). Clearly evident above the basal layer of the epidermis (5) is a layer of live cells (6) firmly linked to one another and the outer layer (3) of dead cells (7), which begin to slough and flake off.

FIG. 3 shows the result of the application of the magnetic composition on the skin at the end of phase a). It can be seen that, after the massage, the magnetic particles (8), thanks to their sufficiently small size and irregular shape, have penetrated homogeneously into the dead surface cells (7) and blackhead (4) and partly into the sebaceous duct (2) as well.

FIG. 4 shows how the skin appears at the opening of the sebaceous duct (2) at the end of phase b). The magnetic particles (8) attracted and removed by the magnet (not portrayed) have carried along with them, in the form of a magnetic pulp (9), the outer dead cells ready to be sloughed off, the blackheads and excess sebum present at the outlet of the sebaceous duct.

The perfect cleansing is thus clearly apparent: the epidermis shows residual outer dead cells still firmly attached (7) and the opening of the sebaceous duct (2) is free of clogging and perfectly functional.

At the end of phase b), consisting in the removal of the magnetic component of the composition of the invention (together with all the polluting materials mixed with it), the residual anhydrous lipogel is removed from the epidermis.

In a particularly preferred embodiment, a gentle massage is performed beforehand (lasting several minutes; for example, from 2 to 10 min, preferably from 3 to 6 min) on the demagnetised skin, so as to permit the active components of the lipogel to complete their anti-inflammatory, soothing, cleansing and emulsifying action and to restore the cement of the corneocytes.

After that, the skin is welshed using a specific tonic suitable for dissolving and removing the lipid components of the lipogel.

Preferably, said tonic is an aqueous-based solution comprising a number of active components having pronounced liophilic, refreshing and soothing characteristics and suitable excipients and vehicles commonly employed in the cosmetic sector.

By way of example, said active components are selected from among: saponins, yucca plant saponins, menthol, hamamelis, lavender, rosemary, gentian, calendula, chamomile, mallow, melissa, aloe, liquorice, aromatising substances, rose and sweet orange.

By way of non-limiting example, in the following Example 5 an illustration is given, in general terms, of the percentage composition by weight of a preferred mixture of active ingredients and excipients useful for achieving the desired tonic according to the invention by suitable mixing of the various components, according to known methods and in suitable mixing means, commonly used in the sector.

EXAMPLE 5

Tonic of the Present Invention—General Example of a Particularly Preferred Mixture of Ingredients (the Percentages in Weight are Relative to the Total Weight of the Final Tonic).

| | |
|---|---|
| "Purified water" | >75% w/w; |
| "*Hamamelis* distilled water" | from 1% to 5% w/w; |
| "Rose distilled water" | from 0.1% to 1% w/w; |
| "Orange distilled water" | from 0.1% to 1% w/w; |
| "Mallow distilled water" | from 0.1% to 1% w/w; |
| "Melissa distilled water" | from 0.1% to 1% w/w; |
| "Vegetable glycerin - official pharmacopeia" | from 0.1% to 1% w/w; |
| "*Yucca* Saponins" | from 0.1% to 1% w/w; |
| "Covafresh II" | from 0.1% to 1% w/w; |
| "*Calendula* mucilage" | from 0.1% to 1% w/w; |
| "Disodium EDTA" | from 0.1% to 1% w/w; |
| "Citricidal" | from 0.1% to 1% w/w. |

Besides freeing the skin from all residual components of the lipogel, the above-described tonic cleans, soothes and refreshes it, lending it a particular softness and lustre, a symptom of good health of the skin itself.

I claim:

1. A skin cleansing magnetic composition consisting of: $Fe_2O_3$ in a quantity between 15 and 25% w/w, relative to the total weight of the composition, said $Fe_2O_3$ having average size of 20-60 μm, and being homogeneously incorporated in an anhydrous lipid-based gel required to reach 100% by weight, relative to the total weight of said skin magnetic composition, said anhydrous lipid-based gel consisting of:

| | |
|---|---|
| Cyclomethicone | from 10% to 26% w/w; |
| $C_{12}$-$C_{15}$ Alkyl Benzoate | from 10% to 25% w/w; |
| *Glycine Soja* Oil | from 10% to 25% w/w; |
| Dicaprylyl Carbonate | from 5% to 10% w/w; |
| PPG-5-Pentaerythrityl Ether | from 5% to 10% w/w; |
| Hydrated Silica | from 5% to 10% w/w; |
| Zinc Oxide | from 5% to 12% w/w; |
| cera alba | from 1% to 10% w/w; |
| Hydrogenated Castor Oil | from 1% to 5% w/w; |
| Quaternium-16-Hectorite | from 1% to 5% w/w; |
| alcohol denaturate | from 0.1% to 1% w/w; |
| Blackcurrant Oil | from 0.1% to 4% w/w; | wherein said skin cleansing magnetic composition after application on the skin and removal of the magnetic particles by means of a magnet or magnetic material, results in a white thick cream that is removable with water or tonic, and once removed it leaves the skin hydrated and free from: redness, irritation or warmth.

* * * * *